United States Patent
Silver et al.

(10) Patent No.: US 6,481,986 B1
(45) Date of Patent: Nov. 19, 2002

(54) VACUUM ADJUSTMENT MECHANISM PARTICULARLY ADAPTED FOR A BREASTPUMP

(75) Inventors: Brian H. Silver, Cary, IL (US); Larry D. Annis, Elgin, IL (US); David A. Bates, Libertyville, IL (US)

(73) Assignee: Medela Holding AG, Baar (CH)

(*) Notice: Subject to any disclaimer, the term of this patent is extended or adjusted under 35 U.S.C. 154(b) by 0 days.

(21) Appl. No.: 09/675,888

(22) Filed: Sep. 29, 2000

Related U.S. Application Data

(63) Continuation-in-part of application No. 09/055,107, filed on Mar. 3, 1998, which is a continuation of application No. 08/510,714, filed on Aug. 3, 1995, now Pat. No. 5,776,098
(60) Provisional application No. 60/157,234, filed on Oct. 1, 1999.

(51) Int. Cl.$^7$ ................................................. F04B 41/00
(52) U.S. Cl. ........................ 417/441; 417/415; 251/208
(58) Field of Search ................................. 417/295, 392, 417/441, 304, 298, 440, 269, 80, 569, 306, 561, 326, 464, 415, 474, 412, 472, 313, 211, 523; 415/216.1; 16/66; 215/335, 11.1, 11.3, 11.5, 228, 212; 251/345, 65, 208, 118, 144.5, 205, 144.6, 319, 199.1, 368, 285; 137/14, 103, 390, 560, 462, 251, 347, 282, 254, 408; 604/22, 65, 119, 318, 346, 30, 32, 241

(56) References Cited

U.S. PATENT DOCUMENTS

| | | |
|---|---|---|
| 823,316 A | 6/1906 | Andersen |
| 1,113,942 A | 10/1914 | Anderson |
| 1,156,202 A | 10/1915 | Barrett |
| 1,184,293 A | 5/1916 | Zeratsky |
| 1,259,309 A | 3/1918 | Somers |

(List continued on next page.)

FOREIGN PATENT DOCUMENTS

| | | |
|---|---|---|
| AU | 121942 | 8/1946 |
| DE | 251810 | 9/1948 |

(List continued on next page.)

OTHER PUBLICATIONS

Nancy Rich, Unknown, Rico Suction Labs, Inc., Catalog—Parts & Supplies, 1, 3.*

(List continued on next page.)

Primary Examiner—Charles G. Freay
Assistant Examiner—John F Belena
(74) Attorney, Agent, or Firm—Baniak Pine & Gannon

(57) ABSTRACT

An improved vacuum adjustment mechanism for controlling airflow into a chamber which is subject to negative pressure, such as the chamber of a diaphragm pump which is generating vacuum for a breast shield assembly, has an air inlet conduit communicating with the chamber. A channel is formed in a base member, with the channel having a longitudinal length and a dimension perpendicular to that length. The perpendicular dimension varies from a minimum to a maximum. The channel has a bottom and is open, such as along a channel top. An airhole is formed in the channel bottom at the point of the maximum dimension. A rotary member is mounted on the base member, and has an internal channel extending across the longitudinal length of the base member channel, and overlies the channel top. The internal channel of the rotary member communicates with an air source, such as ambient air. The rotary member serves to move the internal channel along the longitudinal length of the base member channel, to thereby regulate airflow into the base member channel depending upon where the internal channel is positioned between the minimum and maximum dimensions.

14 Claims, 3 Drawing Sheets

U.S. PATENT DOCUMENTS

| | | | | |
|---|---|---|---|---|
| 1,460,927 | A | 7/1923 | Thompson et al. | |
| 1,509,226 | A | 9/1924 | Brown | |
| 1,596,520 | A | 8/1926 | Eskholme et al. | |
| 1,644,257 | A | 10/1927 | Lasker | |
| 2,060,063 | A | 11/1936 | Frimand | 230/170 |
| 2,222,811 | A | 11/1940 | Dinesen | 230/190 |
| 2,419,795 | A | 4/1947 | Saunders | 128/297 |
| 2,542,505 | A | 2/1951 | Gascoigne | 128/281 |
| 2,545,857 | A | 3/1951 | Perkins et al. | 31/86 |
| 3,238,937 | A | 3/1966 | Stein | 128/40 |
| 3,382,867 | A | 5/1968 | Reaves | 128/38 |
| 3,782,385 | A | 1/1974 | Loyd | 128/281 |
| 3,786,801 | A | 1/1974 | Sartorius | 128/2 F |
| 3,822,703 | A | 7/1974 | Davisson | 128/281 |
| 3,931,795 | A | 1/1976 | Duncan | 119/14.38 |
| 3,977,405 | A | 8/1976 | Yanase | 128/281 |
| 3,990,816 | A | 11/1976 | Köhler et al. | 417/536 |
| 3,998,227 | A * | 12/1976 | Holbrook et al. | 128/276 |
| 4,111,204 | A | 9/1978 | Hessel | 128/276 |
| 4,200,058 | A | 4/1980 | Happel | 119/14.01 |
| 4,249,481 | A | 2/1981 | Adams | 119/14.02 |
| 4,263,912 | A | 4/1981 | Adams | 128/281 |
| 4,311,141 | A | 1/1982 | Diamond | 128/281 |
| 4,323,067 | A | 4/1982 | Adams | 128/281 |
| 4,486,157 | A | 12/1984 | Hayashi | 417/534 |
| 4,558,994 | A | 12/1985 | Viola et al. | 417/295 |
| 4,573,969 | A | 3/1986 | Schlensog et al. | 604/74 |
| 4,583,970 | A | 4/1986 | Kirchner | 604/74 |
| 4,607,596 | A | 8/1986 | Whittlestone et al. | 119/14.02 |
| 4,673,388 | A | 6/1987 | Schlensog et al. | 604/74 |
| 4,680,028 | A | 7/1987 | Stuart | 604/74 |
| 4,710,165 | A | 12/1987 | McNeil et al. | 604/67 |
| 4,726,745 | A | 2/1988 | Adahan | 417/413 |
| 4,740,196 | A | 4/1988 | Powell | 604/75 |
| 4,759,747 | A | 7/1988 | Aida et al. | 604/74 |
| 4,772,262 | A | 9/1988 | Grant et al. | 604/74 |
| 4,789,000 | A | 12/1988 | Aslanian | 137/556 |
| 4,794,915 | A | 1/1989 | Larsson | 128/64 |
| 4,799,922 | A | 1/1989 | Beer et al. | 604/74 |
| 4,813,932 | A | 3/1989 | Hobbs | 604/74 |
| 4,857,051 | A | 8/1989 | Larsson | 604/74 |
| 4,883,464 | A | 11/1989 | Morifuki | 604/74 |
| 4,886,494 | A | 12/1989 | Morifuji | 604/74 |
| 4,892,517 | A | 1/1990 | Yuan et al. | 604/74 |
| 4,909,277 | A | 3/1990 | Vandiver | 137/493.7 |
| 4,929,229 | A | 5/1990 | Larsson | 604/74 |
| 4,941,433 | A | 7/1990 | Hanauer | 119/14.02 |
| 4,961,726 | A | 10/1990 | Richter | 604/74 |
| 4,964,368 | A | 10/1990 | Ball et al. | 119/14.49 |
| 4,964,851 | A | 10/1990 | Larsson | 604/74 |
| 5,007,378 | A | 4/1991 | Larson | 119/14.47 |
| 5,007,899 | A | 4/1991 | Larsson | 607/74 |
| 5,009,638 | A | 4/1991 | Riedweg et al. | 604/74 |
| 5,049,126 | A | 9/1991 | Larsson | 604/74 |
| 5,071,403 | A | 12/1991 | Larsson | 604/74 |
| 5,076,769 | A | 12/1991 | Shao | 417/534 |
| 5,178,095 | A | 1/1993 | Mein | 119/14.47 |
| 5,218,924 | A | 6/1993 | Thompson et al. | 119/14.02 |
| 5,295,957 | A | 3/1994 | Aida et al. | 604/74 |
| 5,304,129 | A | 4/1994 | Forgach | 604/74 |
| 5,308,321 | A | 5/1994 | Castro | 604/74 |
| 5,352,096 | A | 10/1994 | Chi-Wen | 417/12 |
| 5,358,476 | A | 10/1994 | Wilson | 604/74 |
| 5,514,166 | A | 5/1996 | Silver et al. | 604/74 |
| 5,531,712 | A * | 7/1996 | Malcolm et al. | 604/247 |
| 5,571,084 | A | 11/1996 | Palmer | 604/74 |
| 5,586,518 | A | 12/1996 | Carrano | 119/14.51 |
| 5,601,531 | A | 2/1997 | Silver | 604/74 |
| 5,616,125 | A | 4/1997 | Jelks | 604/74 |
| 5,648,606 | A | 7/1997 | Spalding | 73/247 |
| 5,649,809 | A | 7/1997 | Stapelfeldt | 417/63 |
| 5,676,525 | A | 10/1997 | Berner et al. | 417/44.1 |
| 5,720,722 | A | 2/1998 | Lockridge | 604/74 |
| 5,776,098 | A | 7/1998 | Silver et al. | 604/74 |
| 5,947,923 | A * | 9/1999 | Uehara et al. | 604/74 |
| 6,257,847 | B1 | 7/2001 | Silver et al. | 417/415 |

FOREIGN PATENT DOCUMENTS

| | | | |
|---|---|---|---|
| DE | 270694 | 12/1950 | |
| DE | 2658-322 | 6/1978 | A61M/1/06 |
| DE | 33 28 725 A1 | 2/1984 | A61M/1/06 |
| DE | 87 14 995.8 | 2/1988 | A61M/1/06 |
| DK | 158 976 | 5/1957 | |
| EP | 0 123 269 A2 | 4/1984 | A61M/1/06 |
| EP | 0 162 358 A3 | 5/1985 | A61M/1/06 |
| EP | 0 733 376 A2 | 3/1996 | A61M/1/00 |
| GB | 185521 | 9/1922 | |
| GB | 271857 | 5/1927 | |
| GB | 660283 | 11/1951 | |
| GB | 762701 | 12/1956 | |
| GB | 2 082 920 A | 3/1982 | A61M/1/06 |
| GB | 2 127 293 A | 4/1984 | A61M/1/06 |
| IT | 407293 | 9/1944 | |

OTHER PUBLICATIONS

"The Whittlestone Breatmilker" Model Havenwood MK III Operating Manual, date unknown.

"MEDAP" Milchsauger P 6010 . . . Betriebsanleitung Instruction Manual, date unknown.

"Nursing Know–How", Dana Sullivan, date unknown.

Circle of Caring Brochure, Ameda Egnell, circa 1991.

"Breastfeeding A Guide for the Medical Profession", Ruth A. Lawrence, M.D., pp 467–469, Apr. 16, 1986.

Medela Hospital Catalogue, Medela, date unknown.

Breastfeeding: Making an Informed Decision, Kristy Gilson, GFW, May 1997.

"What's New/ Best Seller", Medela Article, Bacon's, May 1997.

"Breastfeeding Made Easier", Great Expectations, Winter, 1996.

"Mom Sings Praises of Mother's Milk", Bacon's, Jan., 1997.

Letter to USPTO from Nancy Rich of Rico Suction Labs, Inc., dated Jan. 3, 2002.

"Everything else is history . . . ", Circle of Caring, Jul./Aug. 1994.

* cited by examiner

VACUUM ADJUSTMENT MECHANISM PARTICULARLY ADAPTED FOR A BREASTPUMP

PRIORITY CLAIM

This application is a continuation-in-part of U.S. Ser. No. 9/055,107 filed Mar. 3, 1998, which is a continuation in part of U.S. Ser. No. 08/510,714 filed Aug. 3, 1995 (now U.S. Pat. No. 5,776,098), and also claims priority to provisional application U.S. Ser. No. 60/157,234 filed Oct. 1, 1999.

FIELD OF THE INVENTION

This invention relates to vacuum adjustment devices, and more particularly to a vacuum adjustment device for a breastpump.

BACKGROUND OF THE INVENTION

This invention was developed with particular application to controlling the vacuum, i.e., negative pressure, within the hood (or shield) of a breastpump. As is well known, vacuum is generated within the downstream part of a funnel-shaped shield within which the breast is received, to draw upon the breast in a manner reminiscent of suckling, and thereby express milk. The milk is typically collected in a bottle or other container, for later use.

There have been mechanisms developed in the past for applying some control over the amount of vacuum (negative pressure) generated at the breast. The present invention was conceived as a considerable improvement over the prior art, providing the user with a continuously variable vacuum adjustment in an easily manipulated device.

SUMMARY OF THE INVENTION

It is accordingly a principal objective of the present invention to provide an improved vacuum adjustment mechanism for controlling airflow into a chamber which is subject to negative pressure, such as the chamber of a diaphragm pump which is generating vacuum for a breast shield assembly. The invention could, however, readily be adapted to some other part of the breastpump.

In one form of the invention, there is an air inlet conduit communicating with the chamber. A channel is formed in a base member, with the channel having a longitudinal length and a dimension perpendicular (e.g., radial) to that length. The perpendicular dimension varies from a minimum to a maximum, which thereby varies the cross-sectional area of the channel. The channel has a bottom and is open, such as along a channel top.

An airhole is formed in the channel, most preferably in the bottom at the point of the maximum dimension. The airhole communicates with the air inlet conduit to the chamber. A rotary member is mounted on the base member. The rotary member has an internal channel, most preferably one having a portion thereof extending across the longitudinal length of the base member channel, and overlies the channel top. The internal channel of the rotary member communicates with an air source, such as ambient air.

The rotary member serves to move its internal channel along the longitudinal length of the base member channel, to thereby regulate airflow into the base member channel depending upon where the internal channel is positioned between the minimum and maximum dimensions. Of course, the internal channel of the rotary member and the base member channel could be reversed with one another, so long as the two are capable of relative rotation.

An embodiment of the inventive vacuum adjustment device furthermore provides an internal channel which has its greatest area (e.g., depth) in the middle, with a decreasing channel dimension on either side thereof. This yields an adjustment feature which is the same regardless of which direction the rotary member is rotated.

The term "perpendicular" relative to the longitudinal length is meant to include any relative dimensional change of the channel or groove. While a change in depth is disclosed in the following embodiments, the dimensional change could be width, or a combination of both length and width.

Other features and advantages of the present invention will become apparent from the detailed description that follows taken in conjunction with the drawings, described below.

DESCRIPTION OF EMBODIMENTS OF THE INVENTION

Figure 1:
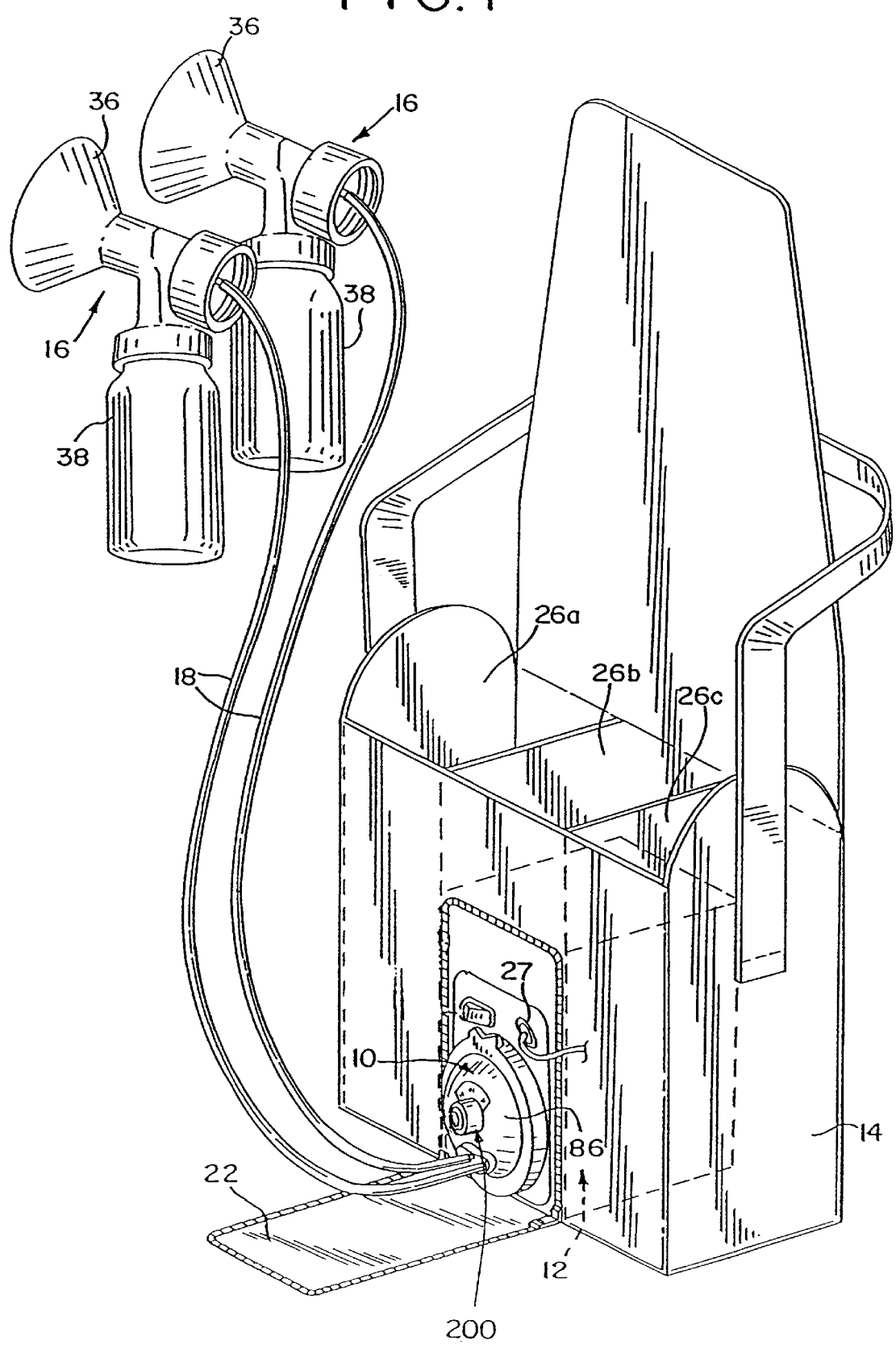
FIG. 1 is a perspective view of a breastpump having a first embodiment of a vacuum adjustment device made in accordance with the present invention.
Figure 2:
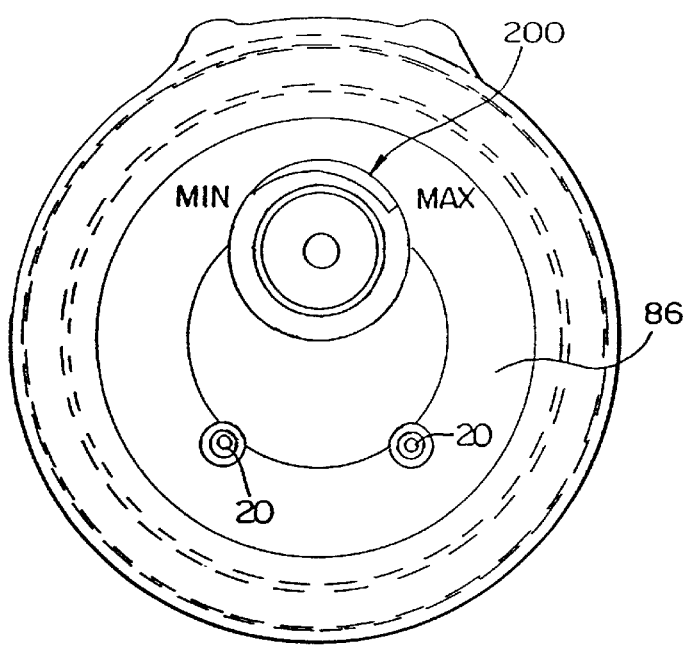
FIG. 2 is a front view of the embodiment of a vacuum adjustment device shown in FIG. 1.
Figure 4:
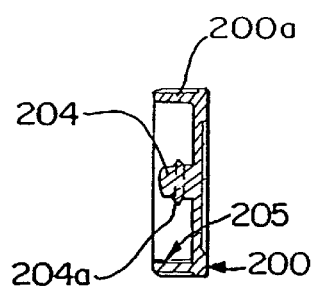
FIG. 4 is a disk valve for use with the rim of FIG. 3.
Figure 3:
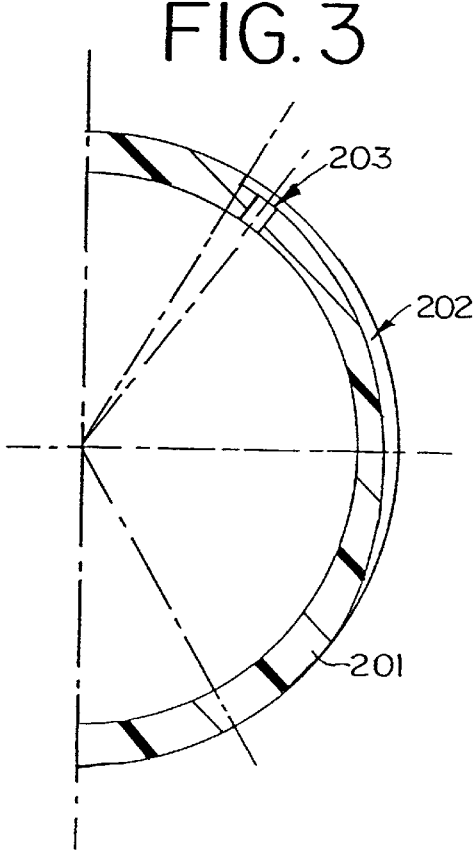
FIG. 3 is an enlarged view of the rim upon which a disk valve rotates in the embodiment of FIG. 2.
Figure 5:
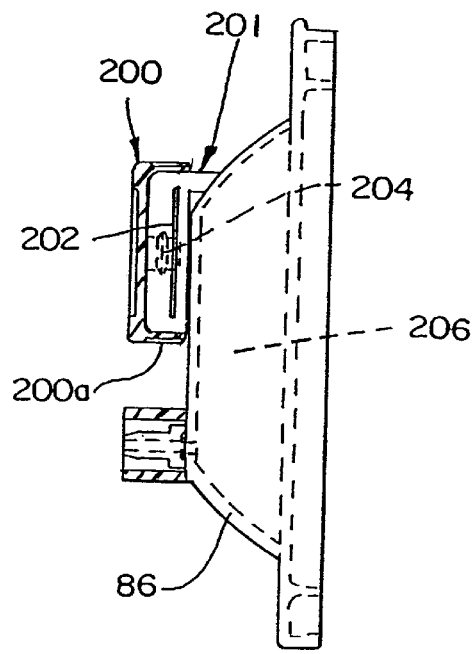
FIG. 5 is a side view partly in section of the embodiment of FIG. 2

Referring to FIG. 1, a diaphragm pump 10 is mounted within a rigid support frame 12. The support frame 12, which is somewhat boxlike, is carried and mounted within a soft carrying case or bag 14. It is shown connected to two breast shield assemblies 16 via tubing 18. Tubing 18 is attached at one end to respective spigots 20 (FIG. 2) via a slip-on fit over the spigots 20. With the tubing 18 removed from the spigots, the diaphragm pump 10 can be closed up within the case 14 via a zippered flap 22.

Case 14 has a number of interior compartments 26a, 26b, 26c, which constitute storage areas, such as for the breast shield assemblies 16, tubing 18, diapers, etc. Case 14 also could include a power source in the form of a battery (not shown) to which a commonly obtainable 12 V DC gear motor is electrically connected. An alternative power source could be an A.C. source (e.g. common 120 VAC service) through a DC converter, as at jack 27 (FIG. 1). The motor, power source and their various electrical connections are all conventional, and well known to those skilled in the art.

The breast shield assemblies 16 are of the type sold by Medela, Inc. under the name MANUALECTRIC, and generally shown in U.S. Pat. Nos. 4,857,051 and 4,929,229, for example. The assemblies 16 have a breast shield 36 associated with a milk bottle 38. A periodic vacuum generated by the pump 10 within the shield 16 serves to extract milk, which is then collected in the bottle 38. Further detail on the forgoing soft-sided breastpump case as well as the diaphragm pumping mechanism used therewith, and its elements and operation, can be obtained from U.S. Pat. No. 5,776,098.

A first form of a vacuum regulation or adjustment device of this invention is shown in FIGS. 2 through 5. In this embodiment, a rotatable regulator disk valve 200 fits upon a rim or collar 201 formed on a rigid cap 86. A channel or recess 202 is formed on the outside of the rim 201. The channel is of constant width but of increasing depth (going from bottom to top as viewed in FIG. 3). A port or hole 203 is the deepest part of the tapered channel 202, and extends through the cap 86 into a chamber 206 defined therein.

Disk valve 200, which can be made of a somewhat flexible rubber material, has a nub 204 that fits within an appropriately sized aperture formed in the rim/cap, with a collar 204a that catches against a sidewall edge defining the aperture to rotatably mount the disk valve 200 in place. On the inside of the disk valve sidewall 200a is a recess 205 which communicates with atmosphere.

Thus, with the disk valve 200 turned so that its recess 205 is located over the shallowest part of the rim channel 202 and furthest from the hole 203, air "leakage" into the cap 86 interior—through the disk valve recess 205 into the rim channel 202 and through the hole 203—is at a minimum. As the disk valve 200 is rotated so that its recess 205 is located at a deeper part of the channel 202, air flows more freely to the hole 203 and into the cap interior, toward a maximum when the recess 205 is over the deepest part of the channel 202 adjacent hole 203. A continuously variable vacuum regulating device is thereby provided.

Figure 6:
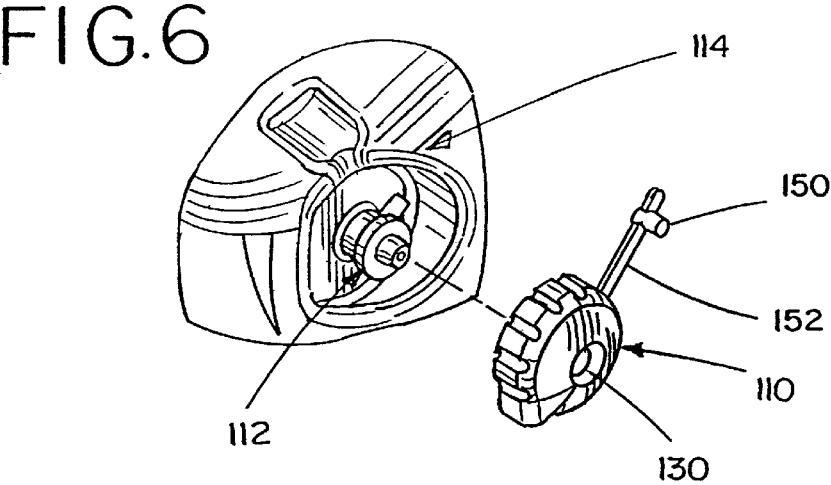
FIG. 6 is an exploded perspective view of part of another breastpump including a second embodiment of a vacuum adjustment device of the present invention.
Figure 7:
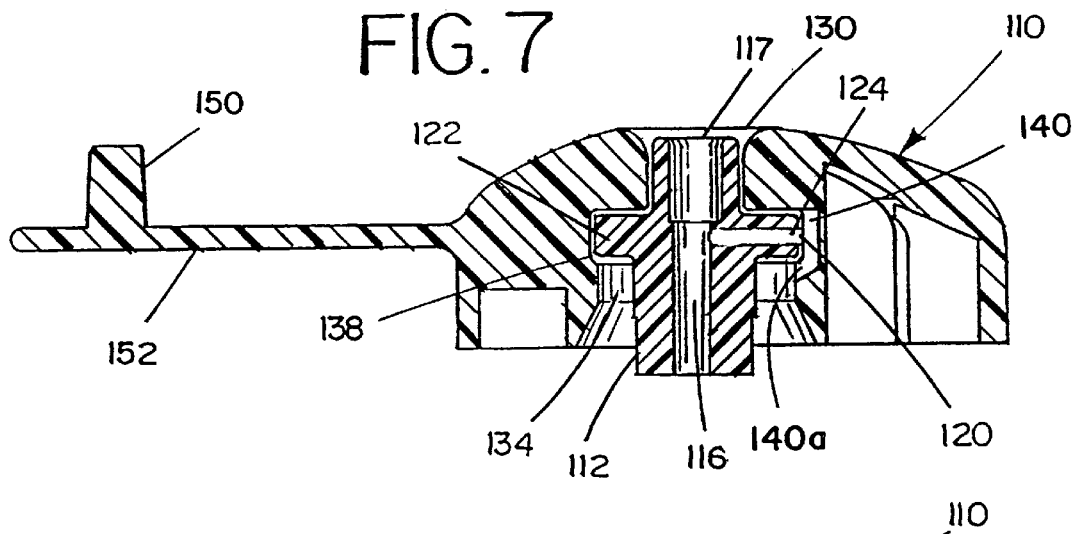
FIG. 7 is a cross-sectional view of the embodiment of FIG. 6 mounted for use.
Figure 8:
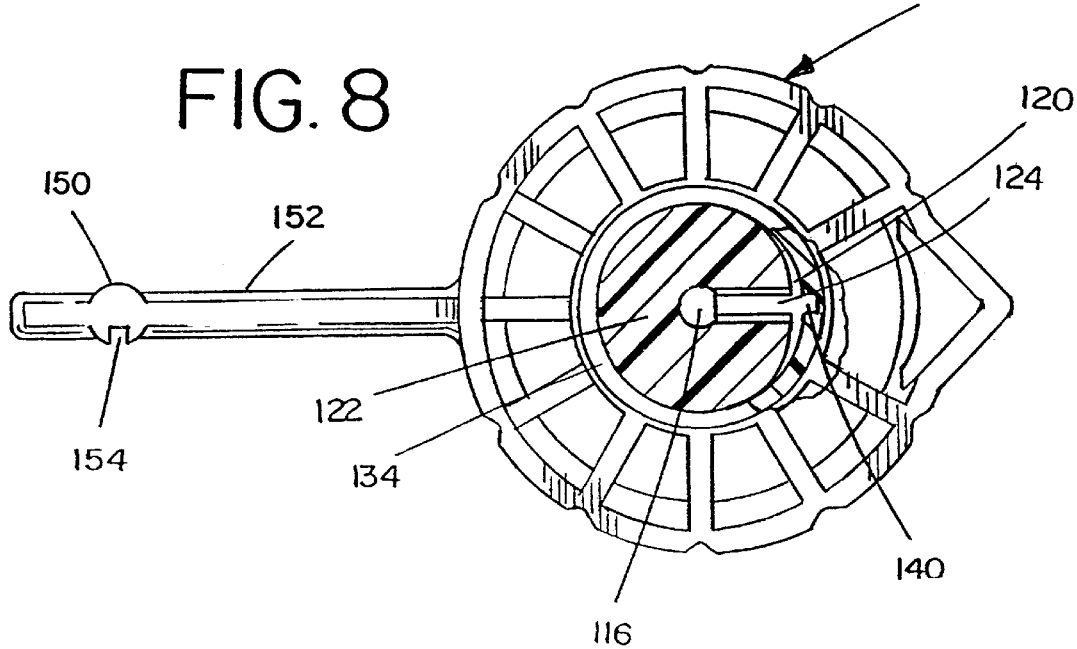
FIG. 8 shows a bottom plan view (i.e., looking up into FIG. 7), partly broken away for clarity, with its insert piece in section.

Now referring to FIGS. 6 through 8, another embodiment is shown. Here, a rotary member or cap 110 is rotatably mounted on a base or insert 112. The insert 112 is fixed to a cover 114 which is part of another type of diaphragm pump assembly (the cover 114 being similar in concept and function to the cap 86).

With reference to FIG. 7, insert 112 has an axial channel 116 which communicates with the interior of the diaphragm pump chamber. Insert 112 has a channel or groove 120 extending around a rim part of a radial disk 122 formed on the insert. The groove 120 has a maximum depth at an airhole 124 (e.g., FIG. 8) which extends into the axial channel 116. Minimum depths are at either end of the groove 120, and as can be seen, the depth varies continuously to either side of the airhole 124.

The cap 110 has a central axial hole 130. Insert 112 is received in a well 134 formed in the cap 110 with the rim of the radial disk 122 located in a race-like portion 138. The cap is made of a generally flexible material to allow easy assembly and air-seals around movable parts. A channel 140 is formed in the cap interior which is perpendicular to and overlies the groove 120. A portion 140a of the channel extends beyond the rim, and communicates with atmosphere.

A plug 150 is attached to a tail piece 152 of the cap 110. Plug 150 has an airhole 154 along its length. Plug 150 is received in the central axial hole 130 of the cap and closes an insert well 117 communicating with axial channel 116, with airhole 154 providing bleed air to the vacuum chamber via channel 116.

Cap 110 when rotated moves the channel 140 along the groove 120. A minimum amount of air will pass to the pump chamber via the airhole 124 with the channel 140 at the minimum depth point of the groove, 120 on either side. A maximum airflow will be directly over the airhole 124, at the maximum depth of the groove 120. The same vacuum adjustment is available either way the cap 110 is rotated.

This ability to change the vacuum the same way in either direction is useful, for example, where there are two vacuum chambers, each located on an opposite side of a pumping mechanism. A mother looking at the pumping mechanism head-on would be able to adjust the vacuum on each side simply by rotating the pointer of the cap up or down, for instance, without regard to clockwise or counterclockwise orientation. A stop, such as the sidewall of the cover 114, or a pin on the cover engaging a part of the internal structure of the cap 110, limits the travel of the cap 110. The vacuum adjustment device thus has a universal application.

It should be appreciated that the present invention is capable of being incorporated in the form of a variety of embodiments, only two of which has been illustrated and described above. The invention may be embodied in other forms without departing from its spirit or essential characteristics. The described embodiments are to be considered in all respects only as illustrative and not restrictive, and the scope of the invention is, therefore, indicated by the appended claims rather than by the foregoing description. All changes which come within the meaning and range of equivalency of the claims are to be embraced within their scope.

What is claimed is:

1. An improved vacuum adjustment mechanism for controlling airflow into a chamber which is subject to negative pressure, comprising:

an air inlet conduit communicating with the chamber;

a channel formed in a base member, said base member channel having a longitudinal length and a dimension perpendicular to said longitudinal length varying from a minimum to a maximum, said base member channel having a channel bottom and being open along a channel top;

an airhole formed in said channel bottom at said maximum dimension, said airhole communicating with said air inlet conduit to the chamber;

a rotary member rotatably mounted on said base member, said rotary member having an internal channel extending across said longitudinal length of said base member channel and overlying said channel top, said internal channel of said rotary member communicating with an air source;

said rotary member when rotated moving said internal channel along said longitudinal length of said base member channel to thereby regulate airflow into said base member channel depending upon where said internal channel is positioned between said minimum and maximum dimensions.

2. An improved vacuum adjustment mechanism for controlling airflow into a chamber which is subject to negative pressure, comprising:

an air inlet conduit communicating with the chamber;

a channel formed in a base member, said base member channel having a longitudinal length and a dimension perpendicular to said longitudinal length varying from a minimum at one end of said base member channel to a maximum and then to another minimum at an opposite end of said base member channel, said base member channel having a channel bottom and being open along a channel top;

an airhole formed in said channel bottom at said maximum dimension, said airhole communicating with said air inlet conduit to the chamber;

a rotary member rotatably mounted on said base member, said rotary member having an internal channel extending across said longitudinal length of said base member channel and overlying said channel top, said internal channel of said rotary member communicating with an air source;

said rotary member when rotated moving said internal channel along said longitudinal length of said base member channel to thereby regulate airflow into said base member channel depending upon where said internal channel is positioned between said minimum and maximum dimensions.

3. An improved vacuum adjustment mechanism for controlling airflow into a chamber, comprising:

a first member having a groove formed on a part thereof, said groove having a longitudinal length and a cross-sectional area perpendicular to said length which varies from a minimum area to a maximum area, said groove having an opening along said length;

an airhole formed in said channel bottom at said maximum area, said airhole communicating with an air inlet conduit to the chamber;

a second member having an air channel formed on a part thereof, said channel communicating with air;

said first and second members being rotatably mounted together, with said air channel extending across said groove;

said first and second members when rotated relative to each other causing said air channel to move along said longitudinal length of said first member groove to thereby regulate airflow into said groove depending upon where said air channel is positioned between said minimum and maximum areas.

4. An improved vacuum adjustment mechanism for controlling airflow into a chamber which is subject to negative pressure, comprising:

an air inlet conduit communicating with the chamber;

a channel formed in a base member, said base member channel having a longitudinal length and a dimension perpendicular to said longitudinal length varying from a minimum to a maximum, said base member channel having a channel bottom and being open along a channel top;

an airhole formed in said channel bottom at about said maximum dimension, said airhole communicating with said air inlet conduit to the chamber;

a rotary member rotatably mounted on said base member, said rotary member having an internal channel communicating with said base member channel and overlying said base member channel top, said internal channel of said rotary member communicating with an air source;

said rotary member when rotated moving said internal channel along said longitudinal length of said base member channel to thereby regulate airflow into said base member channel depending upon where said internal channel is positioned between said minimum and maximum dimensions.

5. An improved vacuum adjustment mechanism for controlling airflow into a chamber which is subject to negative pressure, comprising:

an air inlet conduit communicating with the chamber;

a channel formed in a base member, said base member channel having a longitudinal length and a dimension perpendicular to said longitudinal length varying from a minimum at one end of said base member channel to a maximum and then to another minimum at an opposite end of said base member channel, said base member channel having a channel bottom and being open along a channel top;

an airhole formed in said channel bottom at about said maximum dimension, said airhole communicating with said air inlet conduit to the chamber;

a rotary member rotatably mounted on said base member, said rotary member having an internal channel communicating with said base member channel and overlying said channel top, said internal channel of said rotary member communicating with an air source;

said rotary member when rotated moving said internal channel along said longitudinal length of said base member channel to thereby regulate airflow into said base member channel depending upon where said internal channel is positioned between said minimum and maximum dimensions.

6. An improved vacuum adjustment mechanism for controlling airflow into a chamber, comprising:

a first member having a groove formed on a part thereof, said groove having a longitudinal length and a cross-sectional area along said length which varies from a minimum area to a maximum area, said groove having an opening along said length;

an airhole formed in said groove at about said maximum area, said airhole communicating with an air inlet conduit to the chamber;

a second member having an air channel formed on a part thereof, said channel communicating with air;

said first and second members being rotatably mounted together, with said air channel communicating with said groove;

said first and second members when rotated relative to each other causing said air channel to move along said longitudinal length of said first member groove to thereby regulate airflow into said groove depending upon where said air channel is positioned between said minimum and maximum areas.

7. A breastpump having an improved vacuum adjustment mechanism for controlling airflow into a chamber which is subject to negative pressure, comprising:

an air inlet conduit communicating with the chamber;

a channel formed in a base member, said base member channel having a longitudinal length and a dimension perpendicular to said longitudinal length varying from a minimum to a maximum, said base member channel having a channel bottom and being open along a channel top;

an airhole formed in said channel bottom at about said maximum dimension, said airhole communicating with said air inlet conduit to the chamber;

a rotary member rotatably mounted on said base member, said rotary member having an internal channel communicating with base member channel and overlying said channel top, said internal channel of said rotary member communicating with an air source;

said rotary member when rotated moving said internal channel along said longitudinal length of said base member channel to thereby regulate airflow into said base member channel depending upon where said internal channel is positioned between said minimum and maximum dimensions.

8. The breastpump of claim 7 said base member channel has a dimension perpendicular to said longitudinal length varying from a minimum at one end of said base member channel to a maximum and then to another minimum at an opposite end of said base member channel.

9. The breastpump of claim 7 wherein said dimension perpendicular to said longitudinal length is a depth to said channel.

10. The breastpump of claim 8 wherein said dimension perpendicular to said longitudinal length is a depth to said channel.

11. The breastpump of claim 8 wherein said rotary member internal channel has a slot which extends across said base member channel and overlies said channel top.

12. An improved vacuum adjustment mechanism for a breastpump for controlling airflow into a chamber of the breastpump which is subject to negative pressure, comprising:

a first member having a groove formed on a part thereof, said groove having a longitudinal length and a cross-sectional area along said length which varies from a minimum area to a maximum area, said groove having an opening along said length;

an airhole formed in said groove at about said maximum area, said airhole communicating with an air inlet conduit to the chamber;

a second member having an air channel formed on a part thereof, said channel communicating with air;

said first and second members being rotatably mounted together, with said air channel communicating with said groove;

said first and second members when rotated relative to each other causing said air channel to move along said longitudinal length of said first member groove to thereby regulate airflow into said groove depending upon where said air channel is positioned between said minimum and maximum areas.

13. The breastpump of claim 12 wherein said first member groove has a cross-sectional area varying from a minimum at one end of said groove to a maximum and then to another minimum at an opposite end of said groove.

14. The breastpump of claim 13 wherein said cross-sectional area varies along a depth to said groove, and said second member channel has a slot which extends across said groove and overlies said groove.

* * * * *